(12) United States Patent
Ohnota et al.

(10) Patent No.: US 6,818,776 B2
(45) Date of Patent: Nov. 16, 2004

(54) ALKALI METAL SALT OF THIAZOLIDINE-2, 4-DIONE DERIVATIVE

(75) Inventors: Michiro Ohnota, Nagano (JP); Kazuo Orita, Saitama (JP); Noriyuki Yoshida, Nagano (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 25 days.

(21) Appl. No.: 10/181,432

(22) PCT Filed: Jan. 30, 2001

(86) PCT No.: PCT/JP01/00598
§ 371 (c)(1),
(2), (4) Date: Jul. 25, 2002

(87) PCT Pub. No.: WO01/57007
PCT Pub. Date: Aug. 9, 2001

(65) Prior Publication Data
US 2003/0013749 A1 Jan. 16, 2003

(30) Foreign Application Priority Data
Feb. 1, 2000 (JP) ........................ 2000-023610

(51) Int. Cl.⁷ ............................................ C07D 277/34
(52) U.S. Cl. ..................................................... 548/183
(58) Field of Search ........................................... 548/183

(56) References Cited

U.S. PATENT DOCUMENTS

| 5,308,856 A | 5/1994 | Ohnota et al. |
| 5,342,850 A | 8/1994 | Ohnota et al. |
| 6,030,990 A | * 2/2000 | Maeda et al. ............... 514/369 |

FOREIGN PATENT DOCUMENTS

| EP | 549366 | 6/1993 |
| EP | 855379 | 7/1998 |
| JP | 62-123186 | 6/1987 |
| JP | 8-333355 | 12/1996 |
| JP | 09-48771 | * 2/1997 |
| WO | WO 01/81327 | 11/2001 |

* cited by examiner

Primary Examiner—Joseph K. McKane
Assistant Examiner—Ebenezer Sackey
(74) Attorney, Agent, or Firm—Oblon, Spivak, McClelland, Maier & Neustadt, P.C.

(57) ABSTRACT

The invention provides alkali metal salt of 5-[(2,4-dioxothiazolidin-5-yl)methyl]-2-methoxy-N-[[4-(trifluoromethyl)phenyl]methyl]benzamide and its hydrate. A method has been found, wherein, upon preparing KRP-297, the alkali metal salt of KRP-297 and its hydrate are formed in the reaction system and, after separation and purification, they are freed again from salt, thereby KRP-297 can be advantageously purified industrially for preparation.

8 Claims, No Drawings

ALKALI METAL SALT OF THIAZOLIDINE-2, 4-DIONE DERIVATIVE

TECHNICAL FIELD

The present invention relates to a purifying application and purifying method, using alkali metal salt of 5-[2,4-dioxothiazolidin-5-yl]methyl)-2-methoxy-N-[[4-(trifluoromethyl)phenyl]methyl]benzamide (herein after abbreviated as KRP-297) that improve the diabetes mellitus and hyperlipidemia in the medical field or hydrate of that salt.

BACKGROUND TECHNOLOGIES

The thiazolidine-2,4-dione-based compounds are utilized widely as core element of drugs, and, for the purification thereof, means such as repeated recrystallization with organic solvent and silica gel column chromatography are used. For preparing these compounds in the industrial scale, however, conventional methods have had such difficulties that the yield is low, the removal of impurities is insufficient, or such as harmful solvent must be used in a large quantity.

5-[(2,4-Dioxothiazolidin-5-yl)methyl]-2-methoxy-N-[[4-(trifluoromethyl)phenyl]methyl]benzamide (KRP-297) represented by a following chemical formula (KRP-297)

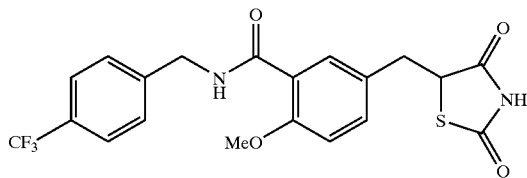

is a compound disclosed in Japanese Unexamined Patent Publication No. Hei 9-48771 as a therapeutic agent of diabetes mellitus and therapeutic agent of hyperlipidemia. It is reported that it has an excellent antihyperglycemic activity (M. Nomura et al, *Bioorg. Med. Chem. Lett.*, 1999, 9, 533), and it has an agonistic action against human peroxisome proliferator-activated receptor (PPAR) (K. Murakami et al, *Diabetes*. 1998, 47, 1841).

Currently, KRP-297 is under clinical trials as a promising therapeutic agent of diabetes mellitus and therapeutic agent of hyperlipidemia.

Hereafter, for massively and continuously preparing KRP-297 with high quality as a drug and high safety containing less impurities, it is required to solve the subjects of improved yield, removal of impurities and reduction of harmful solvents. In particular, the establishment of purifying method of KRP-297, wherein the impurities can be removed efficiently with good reproducibility, will become necessary and indispensable.

DISCLOSURE OF THE INVENTION

As a result of diligent studies to solve the subjects in the industrial preparation of KRP-297 that is promising as a drug, the inventors have found that, by once forming alkali metal salt of KRP-297 after completion of final reaction and by separating and purifying this, followed by freeing, high-purity KRP-297 can be obtained rapidly with good reproducibility, leading to the completion of the invention.

The inventive alkali metal salt of KRP-297 is a novel compound not described in the literatures, and also its usefulness has not yet been known. So far, since it has been known that the thiazolidine-2,4-dione ring is unstable to alkali and the decomposition proceeds in the presence of base, separation of alkali metal salt and industrial application such as purification using it have not been found.

In the invention, upon preparing KRP-297, its alkali metal salt is formed in the reaction system, it is separated and purified, and then freed from that alkali metal salt, thereby high-quality KRP-297 can be prepared in high yield.

The formation of alkali metal salt is conducted by adding aqueous solution or alcoholic solution such as methanol or ethanol of sodium hydroxide or potassium hydroxide to organic solvent such as methylene chloride, isopropyl alcohol or ethyl acetate, in which KRP-297 is dissolved, in a range from 0° C. to 60° C. Immediately after the addition of alkali solution, the sedimentation of salt starts and, thereafter, if stirring for 30 minutes to overnight, the formation and deposition are completed. Then, the precipitates of salt obtained are filtered and washed with small quantity of organic solvent such as isopropyl alcohol or ethyl acetate under suction, thereby obtaining alkali metal salt of KRP-297. The alkali metal salt of KRP-297 can be separated as its hydrate depending on the conditions, or, as the case may be, as its solvating medium. Usually, it can be used even without such separation and purification. Then, this alkali metal salt is dissolved into water or water-containing alcohol and acidic neutralizer such as hydrochloric acid or acetic acid is added to adjust the pH value to a range from 2 to 6, thus making it possible to free KRP-297 as precipitates. The precipitates of KRP-297 obtained are collected by filtration and washed with small quantity of water-containing alcohol, thereby KRP-297 with high purity can be obtained in high yield. Thereafter, if needed, by performing the recrystallization for the purposes of adjustment of crystal form etc., KRP-297 with high quality can be obtained.

According to the method of the invention, because of unnecessity for repeated recrystallization with organic solvent, the complexity of procedure, decrease in yield and, additionally, massive use of recrystallizing solvent and its disposal problems can be solved, hence, not only KRP-297 can be advantageously prepared industrially, but also it is provided as a drug with high purity and high quality.

The inventive alkali metal salt of KRP-297 can be separated as its hydrate depending on the conditions, or, as the case may be, as its solvating medium, which are all included in the invention. Moreover, since KRP-297 has one asymmetric carbon atom on the thiazolidine-2,4-dione ring, it can form two optical isomers, but it goes without saying that the optical isomers and their mixtures are included in that alkali salt.

EXAMPLE

In following, the invention will be illustrated based on concrete examples, but the invention is not confined to these examples.

Example 1

KRP-297 (2.20 g) was suspended in 2-propanol (80 mL). The mixture was heated and dissolved. A solution of sodium hydroxide (213 mg) in water (2.5 mL) was added at 70° C. After addition, the solution was cooled to 50° C. The precipitates were collected by suction and washed with 2-propanol (10 mL), and dried at 30° C. in vacuo to give sodium salt of KRP-297 (1.59 g, 67.5%) as hemihydrate.

Melting point: 273.0~275.0° C.

$^1$H NMR (400 MHz, $d_6$-DMSO): δ 2.69 (1H, dd, J=14.2, 10.3 Hz), 3.30~3.35 (1H, m), 3.78 (3H, s), 4.11 (1H, dd, J=10.3, 3.9 Hz), 4.57 (2H, d, J=5.9 Hz), 7.05 (1H, d, J=8.8 Hz), 7.31 (1H, dd, J=8.3, 2.4 Hz), 7.53~7.56 (3H, m), 7.70 (2H, d, J=7.8 Hz), 8.80 (1H, t, J=5.9 Hz).

MS (FAB) m/z: 461[M+1]$^+$.

Anal.: Calcd. for $C_{20}H_{16}F_3N_2NaO_4S \cdot \frac{1}{2}H_2O$: C, 51.17; H, 3.65; N, 5.97%. Found: C, 51.15; H, 3.41; N, 5.93%.

Example 2

KRP-297 (30.0 g) were suspended in methylene chloride (193 mL). Triethylamine (6.93 g) was added, and the mixture was dissolved. A solution of potassium hydroxide (4.52 g) in methanol (69 mL) was added dropwise under 5° C. After stirring for 1.5 h at the same temperature, the precipitates were collected by suction and washed with methylene chloride (58 mL), and dried at 30° C. in vacuo to give potassium salt of KRP-297 (30.5 g, 93.5%) as monohydrate.

Melting point: 199~200° C.

$^1$H NMR (400 MHz, $d_6$-DMSO): δ 2.69 (1H, dd, J=13.7, 10.3 Hz), 3.17 (methanol), 3.30~3.34 (1H, m), 3.87 (3H, s), 4.10 (1H, dd, J=10.3, 3.9 Hz), 4.57 (2H, d, J=6.4 Hz), 7.05 (1H, d, J=8.8 Hz), 7.31 (1H, dd, J=8.8, 2.4 Hz), 7.53~7.55 (3H, m), 7.70 (2H, d, J=8.3 Hz), 8.80 (1H, t, J=6.4 Hz).

MS(FAB) m/z: 477[M+1]$^+$.

Anal: Calcd. for $C_{20}H_{16}F_3N_2KO_4S \cdot \frac{1}{4}CH_3OH \cdot \frac{1}{4}H_2O$; C: 49.73; H:3.61; N:5.73%. Found; C: 49.44; H:3.31; N:5.88%.

Example 3

5-[(2.4-dioxothiazolidin-5-yl)methyl]-2-methoxybenzoic acid (5.00 g) and triethylamine (4.50 g) were added in 2-propanol (35 mL) and dissolved. Ethyl chlorocarbonate (2.12 g) were added dropwise at −5~0° C. After stirring for 10 minutes at −5~0° C., a solution of 4-trifluoromethylbenzylamine (3.27 g) in 2-propanol (15 mL) was added dropwise at −5~0° C. The reaction mixture was heated to 25° C. and stirred for 1 hour at 25~35° C., and subsequently heated to 60° C. 24.5% aqueous sodium hydroxide solution (4.83 mL) was added, and the solution was cooled to 3° C. The deposited sodium salt were collected by suction and washed with 2-propanol (15 mL).

The sodium salt was added to a mixture of water(78 mL) and 2-propanol (59 mL) and dissolved. The solution was adjusted to pH 6.95 with 1 mol/L hydrochloric acid. After cooling to 6° C., precipitates were collected by suction and washed with water(23 mL) and dried at 40° C. to give crude products (6.59 g, 84.6%).

The crude products were recrystallized from 90% ethanol (132 mL) and dried at 40° C. in vacuo to give 5-[(2,4-dioxothiazolidin-5-yl)methyl]-2-methoxy-N-[[4-(trifluoromethyl)phenyl]methyl]benzamide (6.02 g, 77.3%).

Example 4

5-[(2,4-dioxothiazolidin-5-yl)methyl]-2-methoxybenzoic acid (1.50 g) were dissolved in a mixture of 2-propanol (10.5 mL) and triethylamine (1.35 g), and ethyl chlorocarbonate (580 mg) were added dropwise at −5~0° C. After stirred for 30 minutes, a solution of 4-trifluoromethylbenzylamine (900 mg) in 2-propanol (4.0 ml) was added dropwise at −7~0° C., and the mixture was stirred for 2 h at room temperature. The solvent was removed in vacuo, and ethyl acetate (15 mL) was added. The solution was washed with water and dried over sodium sulfate. The solution was concentrated to about 15 mL in vacuo, and the solution of potassium hydroxide in methanol (1 mol/L, 5.3 mL) was added. The mixture was stirred for 20 minutes on ice-cooling. The precipitates were collected by suction and washed with ethyl acetate, and dried in vacuo to give potassium salt (2.05 g, 80.7%) as white powder.

This potassium salt was dissolved in a mixture of water (20.5 mL) and 2-propanol (20.5 mL), and 1 mol/L hydrochloric acid was added dropwise at 3~5° C. to adjust the solution to pH 2. After stirred for 1.5 h on ice-cooling, the precipitates were collected by suction and washed with water, to give wet crude crystals. The wet crude crystals were added in a mixture of 2-propanol (40 mL) and water (9 mL) and dissolved on heating. The solution was filtered while hot, and the filter was washed with a mixture of 2-propanol (3.0 mL) and water (0.8 mL). The filtrate was heated for dissolution of precipitates, and the solution was stirred for 16.5 h at room temperature. The precipitates were collected by suction and dried in vacuo to give KRP-297 (1.61 g, 69.0%) as white powder.

Example 5

5-[(2,4-dioxothiazolidin-5-yl)methyl]-2-methoxybenzoic acid (1.50 g) were dissolved in a mixture of acetone (10.5 mL) and triethylamine (1.35 g), and ethyl chlorocarbonate (580 mg) were added dropwise at −5~−1° C. on cooling. After stirred for 15 minutes, a solution of 4-trifluoromethylbenzylamine (980 mg) in acetone (4.0 ml) was added dropwise at −10~−4° C., and the mixture was stirred for 75 minutes at room temperature. The solvent was removed in vacuo, and ethyl acetate (10 mL) was added to the residue. The solution was washed with water and dried over sodium sulfate. The solution was concentrated to about 15 mL in vacuo, and the solution of potassium hydroxide in methanol (1 mol/L, 5.3 mL) was added. The mixture was stirred for 20 minutes on ice-cooling. The precipitates were collected by suction and washed with ethyl acetate, and dried in vacuo to give potassium salt (2.19 g, 86.2%) as white powder.

This potassium salt was dissolved in a mixture of water (22.0 mL) and 2-propanol (22.0 mL), and 1 mol/L hydrochloric acid was added dropwise to adjust the solution to pH 2. After stirred for 2 h on ice-cooling, precipitates were collected by suction and washed with water, to give wet crude crystals. The wet crude crystals were added in a mixture of 2-propanol (40 mL) and water (8 mL) and dissolved on heating and filtered while hot, and the filter was washed with a mixture of 2-propanol (3.0 mL) and water (0.8 mL). The filtrate was heated for dissolution of precipitates, and the solution was stirred for 19 h at room temperature. The precipitates were collected by suction and dried in vacuo to give KRP-297 (1.75 g, 75%) as white powder.

Example 6

5-[(2,4-dioxothiazolidin-5-yl)methyl]-2-methoxybenzoic acid (5.20 kg) were dissolved in a mixture of 2-propanol (36.6 L) and triethylamine (4.68 kg), and ethyl chlorocarbonate (2.11 kg) were added dropwise at −5~0° C. After stirred for 10 minutes, a solution of 4-trifluoromethylbenzylamine (3.24 kg) in 2-propanol (15.6 L) was added dropwise at −5~0° C., and the mixture was heated to 25° C. and stirred for 1 h at 25~30° C. 2-Propanol (20.8 L) was added, and subsequently the 24.5% aqueous sodium hydroxide solution(5.0 L) was added. The mixture was stirred for 1.5 h under 10° C. The precipitates were collected by filtration and washed with 2-propanol (15.6 L) to give sodium salt (7.78 kg (91.4%) as conversion value from the value of loss on drying).

This sodium salt was dissolved in a mixture of water (77.8 L) and 2-propanol (72.9 L), and 1 mol/L hydrochloric acid was added dropwise at 0~10° C. to adjust the solution to pH 2. After stirred for 1.5 h at 0~10° C., precipitates were collected by centrifuge and washed with water (81.1 L), to give wet crude products (6.12 kg (75.5%) as conversion value from the value of loss on drying). The wet crude products were added in a mixture of 2-propanol (122 L) and water (28.6 L) and dissolved over 70° C. The solution was filtered while hot, and the filter was washed with a mixture of 2-propanol (9.8 L) and water (2.4 L). The filtrate was cooled to room temperature and stirred for 15 h. The precipitates were collected by filtration and washed with 2-propanol (18.4 L) and dried at 40° C. in vacuo to give KRP-297 (5.32 kg, 65.6%).

Utilizability in the Industry

This invention relates to alkali metal salt of KRP-297 or its hydrate and to purifying application and purifying method of KRP-297 using it. If using the inventive alkali metal salt in the preparative process, because of unnecessity for repeated recrystallization with organic solvent, the complexity of procedure, decrease in yield and, additionally, massive use of recrystallizing solvent and its disposal problems can be solved, hence, not only KRP-297 can be advantageously prepared industrially, but also it is provided as a drug with high purity and high quality.

What is claimed is:

1. Method of purifying 5-[(2,4-dioxothiazolidin-5-yl)methyl]-2-methoxy-N-[[4-(trifluoromethyl)phenyl]methyl]benzamide, characterized in that aqueous solution or alcoholic solution of alkali hydroxide is added to an organic solvent dissolved 5-[(2,4-dioxothiazolidin-5-yl)methyl]-2-methoxy-N-[[4-(trifluoromethyl)phenyl]methyl]benzamide, thereby, forming and sedimenting alkali metal salt of 5-[(2,4-dioxothiazolidin-5-yl)methyl]-2-methoxy-N-[[4-(trifluoromethyl)phenyl]methyl]benzamide or hydrate of that salt.

2. A method of purifying 5-[(2,4-dioxothiazolidin-5-yl)methyl]-2-methoxy-N-[[4-(trifluoromethyl)phenyl]methyl]benzamide, the method comprising dissolving 5-[(2,4-dioxothiazolidin-5-yl)methyl]-2-methoxy-N-[[4-(trifluoromethyl)phenyl]methyl]benzamide in an organic solvent to form an organic solution;

adding to the organic solution an aqueous or alcoholic solution comprising an alkali hydroxide to form a mixed solution;

precipitating from the mixed solution an alkali metal salt;

separating the alkali metal salt from the mixed solution;

dissolving the metal salt in water or aqueous alcohol to form a mixture;

adding an acidic neutralizer to the mixture to adjust the pH of the mixture to a range of from 2 to 6; and freeing from the alkali metal salt the 5-[(2,4-dioxothiazolidin-5-yl)methyl]-2-methoxy-N-[[4-(trifluoromethyl)phenyl]methyl]benzamide.

3. The method according to claim 2, wherein the organic solvent is selected from the group consisting of methylene chloride, isopropyl alcohol and ethyl acetate.

4. The method according to claim 2, wherein the 5-[(2,4-dioxothiazolidin-5-yl)methyl]-2-methoxy-N-[[4-(trifluoromethyl)phenyl]methyl]benzamide is dissolved in the organic solvent at a temperature in a range of from 0° to 60° C.

5. The method according to claim 2, wherein the aqueous or alcoholic solution is an alcoholic solution; and the alcoholic solution comprises an alcohol selected from the group consisting of methanol and ethanol.

6. The method according to claim 2, wherein the alkali hydroxide is selected from the group consisting of sodium hydroxide and potassium hydroxide.

7. The method according to claim 2, wherein the acidic neutralizer is selected from the group consisting of hydrolic acid and acetic acid.

8. A method of using an alkali metal salt of 5-[(2,4-dioxothiazolidin-5-yl)methyl]-2-methoxy-N-[[4-(trifluoromethyl)phenyl]methyl]benzamide or hydrate of that salt, the method comprising dissolving the metal salt in water or aqueous alcohol to form a mixture;

adding an acidic neutralizer to the mixture to adjust the pH of the mixture to a range of from 2 to 6; and freeing from the alkali metal salt or hydrate of that salt 5-[(2,4-dioxothiazolidin-5-yl)methyl]-2-methoxy-N-[[4-(trifluoromethyl)phenyl]methyl]benzamide.

* * * * *